United States Patent
Lai

[19]

[11] Patent Number: 5,858,402
[45] Date of Patent: Jan. 12, 1999

[54] METHODS FOR IN VIVO REDUCTION OF CYANIDE LEVELS AND COMPOSITIONS USEFUL THEREFOR

[75] Inventor: Ching-San Lai, Encinitas, Calif.

[73] Assignee: Medinox, Inc., San Diego, Calif.

[21] Appl. No.: 799,755

[22] Filed: Feb. 11, 1997

[51] Int. Cl.$^6$ .......................... A61K 9/127; A61K 31/27; A61K 31/55; A61K 31/44

[52] U.S. Cl. ............................ 424/450; 424/43; 424/434; 424/435; 424/436; 514/476; 514/491; 514/212; 514/332; 514/336; 514/514; 514/351; 514/422; 514/428

[58] Field of Search ..................... 424/450, 43, 434–436; 514/476, 491, 212, 332, 336, 351, 422, 428, 937

[56] References Cited

U.S. PATENT DOCUMENTS

| | | | |
|---|---|---|---|
| 4,160,452 | 7/1979 | Theeuwes | 128/260 |
| 4,256,108 | 3/1981 | Theeuwes | 128/260 |
| 4,265,874 | 5/1981 | Bosen et al. | 424/15 |
| 5,357,703 | 10/1994 | Lai | 424/9 |

OTHER PUBLICATIONS

Hanesel et al. Pharm. Ztg 118 (26) pp. 987–990, (English Abst & Gen Article, 1973.

Baskin et al., "The Antidotal Action of Sodium Nitrite and Sodium Thiosulfate Against Cyanide Poisining" *J. Clin. Pharmacol.*, 32:368–375 (1992).

Bates et al., "Nitric Oxide Generation from Nitroprusside by Vascular Tissue" *Biochem. Pharmacol.*, 42:S157–S165 (1991).

Dreisbach and Robertson, "Handbook of Poisoning: Prevention, Diagnosis and Treatment," 12th edn., Appleton & Lange, Los Altos, CA, p. 251 (1987).

Houeto et al., "Relation of blood cyanide to plasma cyanocobalamin concentration after a fixed dose of hydroxocobalamin in cyanide Poisoning" *Lancet*, 346:605–608 (1995).

Kanthasamy et al., "Dopaminergic Neurotoxicity of Cyanide: Neurochemical, Histological, and Behavioral Characterization" *Toxicol. App. Pharmacol.*, 126:156–163 (1994).

Kowaluk et al., "Metabolic Activation of Sodium Nitroprusside to Nitric Oxide in Vascular Smooth Muscle" *J. Pharm. Exp. Therap.*, 262(3):916–922 (1992).

Lai and Komarov, "Spin trapping of nitric oxide produced in vivo in septic–shock mice" *FEBS Lett.*, 345:120–124 (1994).

Myers et al., "Comparison of Tests for Detecting Leaks in the Low–Pressure System of Anesthesia Gas Machines" *Anasth. Analg.*, 84:179–184 (1997).

Ruokonen et al., "Regional blood flow and oxygen transport in patients with the low cardiac output syndrome after cardiac surgery" *Crit. Care Med.*, 21(9):1304–1311 (1992).

Sadoff et al., "Rapid Death Associated With Laetrile Ingestion" *J. Am. Med. Assoc.*, 239(15):1532 (1978).

(List continued on next page.)

*Primary Examiner*—Gollamudi S. Kishore
*Attorney, Agent, or Firm*—Gray, Cary, Ware & Freidenrich; Stephen E. Reiter

[57] ABSTRACT

In accordance with the present invention, there are provided in vivo methods for the reduction of cyanide levels. The present invention employs a scavenging approach whereby cyanide is bound in vivo to a suitable scavenger. The resulting complex renders the cyanide harmless, and is eventually excreted in the urine of the host. Further in accordance with the present invention, there are provided compositions and formulations useful for carrying out the above-described methods.

13 Claims, 2 Drawing Sheets

OTHER PUBLICATIONS

Scharf et al., "Comparison of Methemoglobin Formers in Protection Against the Toxic Effects of Cyanide" *Gen. Pharmacol.*, 23(1):19–25 (1992).

Shinobu et al., "Sodium N–Methyl–D–glucamine Dithiocarbamate and Cadium Intoxication" *Acta Pharmacol et Toxicol.*, 54:189–194 (1984).

Solomonson, L. P., "Cyanide as a Metabolic Inhibitor" *Cyanide in Biology*, (B. Vennesland et al., Eds.) Academic Press, New York. pp. 11–28 (1981).

Vessy and Cole, "Blood Cyanide and Thiocyanate Concentrations Produced by Long–Term Therapy With Sodium Nitroprusside" *Br. J. Anaeth.*, 57:148–155 (1985).

Yamamoto, "Protection against cyanide–induced convulsions with α–ketoglutarate" *Toxicol.*, 61:221–228 (1990).

METHODS FOR IN VIVO REDUCTION OF CYANIDE LEVELS AND COMPOSITIONS USEFUL THEREFOR

FIELD OF THE INVENTION

The present invention relates to methods for reducing cyanide levels in mammals. In a particular aspect, the present invention relates to methods for reducing cyanide levels in mammals by administration thereto of physiologically compatible compounds which are capable of binding cyanide. Invention methods are useful, for example, in hosts subject to cyanide toxicity and/or cyanide poisoning. In a further aspect, the present invention relates to compositions and formulations useful in the methods disclosed herein.

BACKGROUND OF THE INVENTION

Cyanide (CN), a fast acting toxic compound, is frequently used in suicides, homicide, and chemical warfare (see, for example, Salkowski et al., in Vet. Hum. Toxicol. 36:455–466 (1994) and Borowitz et al., in B. Somani (Ed.), Chemical Warfare Agents, Academic Press, New York, pp.209–236 (1992)). Cyanide toxicity can arise from a variety of sources, e.g., from inhalation of smoke produced by the pyrolysis of plastics or nitrile-based polymer fibers, materials that are commonly used in construction and for furniture manufacture. Cyanide toxicity can also occur from ingestion of plant extracts containing cyanogenic glycosides (such as cassava), or from inhalation of airborne vapors encountered in industrial or occupational settings (for example, during electroplating). Clinically, the release of cyanide from sodium nitroprusside (see, for example, Vessy and Cole, in Br. J. Anaesth. 57:148–155 (1985)) and laetrile (see, for example, Sadoff et al., in J. Am. Med. Assoc. 239:1532 (1978)) can create a life-threatening situation.

Acute cyanide poisoning of mammals is characterized by convulsion, uncoordinated movement, decreased motor activity, coma and respiratory arrest, symptoms indicating that the brain is one major target site for cyanide. This type of neurotoxicity is now known to be caused by cyanide-induced depletion of dopamine (see, for example, Kanthasamy et al., in Toxicol. App. Pharmacol. 126:156–163 (1994)) and by an increase in calcium in the brain (see, for example, Yamamoto, in Toxicol. 61:221–228 (1990)). The systemic toxic effect of cyanide has been attributed mainly to its binding to the ferric iron in cytochrome c oxidase, the terminal oxidase enzyme of the mitochondrial respiratory chain. The reaction forms a stable but reversible complex and subsequently disrupts cellular energy production. The reduction of cellular oxygen consumption results in an increase in venous oxygen partial pressure ($PO_2$).

The classic antidotal action for cyanide poisoning, introduced by Chen et al. in 1933 (see, for example, Chen et al., Proc. Soc. Exp. Biol. Med. 31:250–252 (1933)), involves inhalation of amyl nitrite, followed by intravenous injection of sodium nitrite and sodium thiosulfate. This procedure is still used clinically worldwide, including the United States (see, for example, Dreisbach, in Handbook of poisoning: Diagnosis and treatment, 12th edn., Lange Med. Publications., Los Altos, Calif., p.251 (1987)). In essence, in this method, oxyhemoglobin in red blood cells in the circulation is converted into methemoglobin by chemical reaction with nitrites. Methemoglobin then binds cyanide, thereby removing it from the circulation. Sodium thiosulfate is used as a sulfur donor to allow the formation of thiocyanate, through the reaction catalyzed by rhodanese enzyme (see, for example, Baskin et al., in J. Clin. Pharmacol. 32:368–375 (1992)).

There are, however, major drawbacks of the nitrite/sodium thiosulfate method. For example, the rate of methemoglobin formation is quite slow, taking up to 20 minutes to produce sufficient amounts of methemoglobin. Moreover, the formation of methemoglobin compromises the oxygen-carrying capacity of red blood cells. This is particularly undesirable for victims of smoke inhalation, as adequate ventilation and blood oxygenation are particularly crucial for survival in such situations. Furthermore, hypotension induced by the treatment (i.e., nitrite-induced hypotension) can be life-threatening.

In addition to nitrites, a variety of chemical agents have been used to induce methemoglobinemia as a treatment for cyanide poisoning. These include primaquine phosphate, 6-methoxy-8- (6-diethylamino-hexylamino) lepidine dihydrochloride, p-aminooctoyl-phenone, p-aminopropiophenone, hydroxylamine, 4-dimethylaminophenol, and the like (see, for example, Scharf et al., in Gen. Pharmacol. 23:19–25 (1992)). Although the rates of methemoglobin formation induced by these agents are faster than those produced by nitrites, the same problems as described above are common to all methemoglobin formers.

Recently, hydroxocabalamin, vitamin $B_{12}$, has been shown to be effective in the treatment of cyanide poisoning in smoke inhalation (see, for example, Houeto et al., in Lancet 346:605–608 (1995)). Hydroxocabalamin is a cobalt-containing compound for which only minute amounts are needed physiologically. Clinical use of hydroxocabalamin for the treatment of cyanide poisoning, however, requires the use of 5 grams per patient. Such high levels of hydroxocabalamin are not only expensive but also potentially toxic because extremely high circulatory levels of cobalt are produced.

Nitroprusside (SNP for sodium nitroprusside) is widely used as a source of nitric oxide for the treatment of severe hypertension, induction of arterial hypotension during surgery, the reduction of after-load after myocardial infarction and during severe congestive heart failure (see, for example, Rokonen et al., in Crit. Care Med. 21:1304–1311 (1993) and Sellke et al., in Circulation 88:II395–II400 (1993)). A nitroprusside molecule ($NaFe(CN)_5NO.2H_2O$) contains one nitric oxide and five cyanide groups. Upon intravenous infusion, nitroprusside is known to be metabolized through one-electron reduction to release nitric oxide, a potent vasodilator, which exerts the desired antihypertensive effect (see, for example, Bates et al., in Biochem. Pharmacol. 42:S157–S165 (1991) and Kowaluk et al., in J. Pharm. Exp. Therap. 262:916–922 (1992)). Unfortunately, however, upon release of nitric oxide, SNP further decomposes to release five cyanide groups which can produce life-threatening cyanide poisoning in patients. This high level of cyanide release occurs very commonly in high dose or prolonged therapy with nitroprusside.

Current clinical treatment of nitroprusside-induced cyanide toxicity is, unfortunately, limited to the use of amyl nitrite and sodium nitrite (for the conversion of hemoglobin to methemoglobin) or vitamin $B_{12}$. The many drawbacks of using these agents have been set forth above.

Accordingly, there is still a clear need in the art to develop effective, rapid acting, non-toxic antidotes for cyanide poisoning.

BRIEF DESCRIPTION OF THE INVENTION

In accordance with the present invention, methods have been developed for the in vivo reduction of cyanide levels.

The present invention describes the in vivo use of chelating complexes such as N-methyl-D-glucamine dithiocarbamate-ferrous iron complex [(MGD)$_2$/Fe], which tightly binds cyanide to prevent its toxic effects. Dithiocarbamates are a class of low molecular-weight sulphur-containing compounds that are effective chelators (see, for example, Shinobu et al., Acta Pharmacol et Toxicol. 54:189–194 (1984)). For example, diethyldithiocarbamate (DETC) is used clinically for the treatment of nickel poisoning.

Recently, it was found that MGD chelates with ferrous iron as a two-to-one [(MGD)$_2$/Fe] complex, which in turn interacts strongly with nitric oxide, forming a stable and water-soluble complex in aqueous solution, i.e., [(MGD)$_2$/Fe-NO] complex (see, for example, Lai & Komarov, FEBS Lett. 345:120–124 (1994)). The latter complex gives rise to a sharp three-line spectrum with $g_{iso}$=2.04, characteristic of a nitrosyl-Fe-dithiocarbamate complex which can readily be detected by EPR spectroscopy at ambient temperatures. This method of detecting NO in body fluids in real time has recently been described by Lai in U.S. Pat. No. 5,358,703. In addition, administration of at dithiocarbamates, with or without added iron, has been demonstrated to be effective in reducing in vivo nitric oxide levels in mammals with inflammatory or infectious diseases, as recently described by Lai in U.S. Ser. No. 08/459,518, now pending.

In contrast to the approaches described in the prior art (see references cited above), the present invention employs a scavenging approach whereby cyanide is bound in vivo to a suitable cyanide binding chelate. The resulting complex renders the cyanide harmless, and is eventually excreted in the urine of the host. Further in accordance with the present invention, there have been developed compositions and formulations useful for carrying out the above-described methods.

BRIEF DESCRIPTION OF THE FIGURE

FIG. 1A provides a spectrum of the [(MGD)$_2$/Fe] complex. An aliquot (40 μl) of ferric sulfate (10 mM) in water was added to 2 ml of water containing 1 mM MGD. Water was used as the control. The spectrum was recorded from 400–600 nm. Note that the [(MGD)$_2$/Fe] complex showed an intense charge transfer peak at 508 nm.

FIG. 1B provides a spectrum of the [(MGD)$_2$/Fe] complex in the presence of sodium cyanide. An aliquot (40 μl) of sodium cyanide (10 mM) in water was added to 2 ml water containing 1 mM MGD and 0.2 mM Fe$^{3+}$. Note the disappearance of the charge transfer peak at 508 nm.

DETAILED DESCRIPTION OF THE INVENTION

Figure 1A:
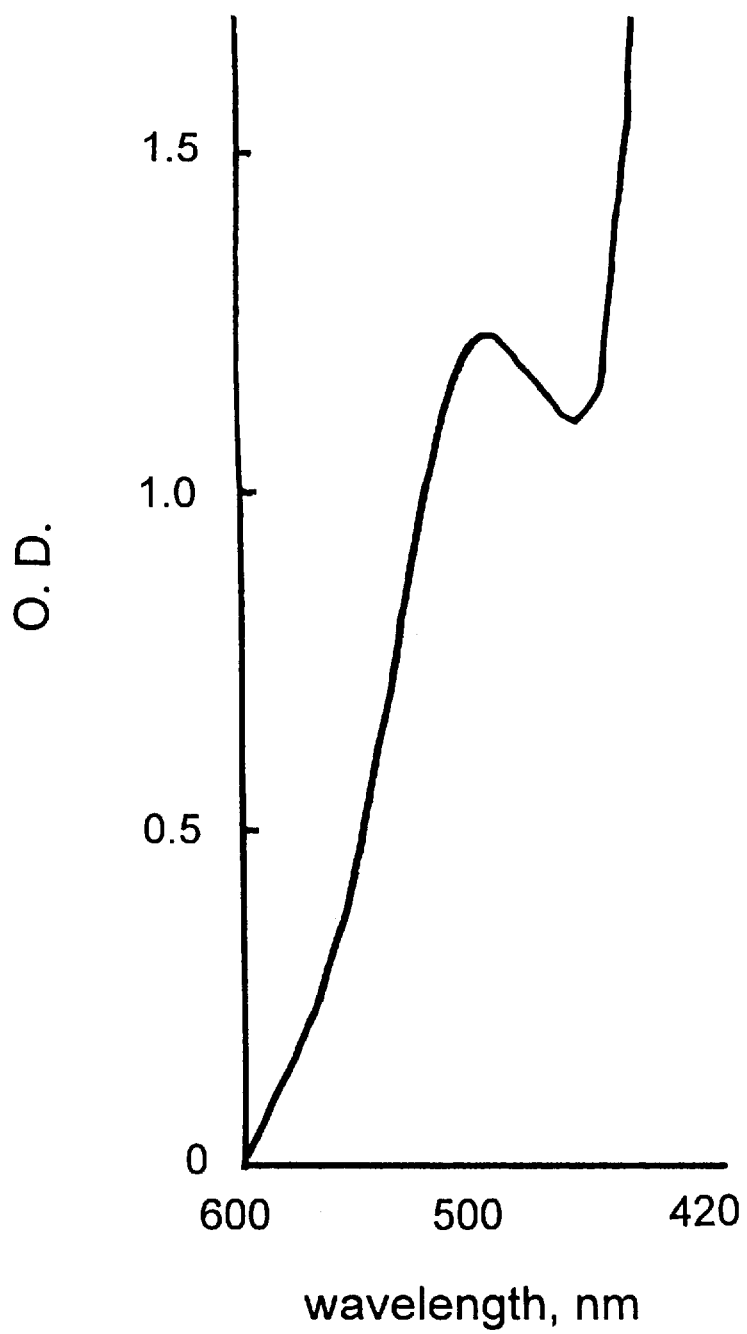
FIGS. 1A and 1B collectively illustrate the effect of cyanide addition on the visible absorption spectrum of the chelator-iron complex, N-methyl-D-glucamine dithiocarbamate (MGD) and iron (Fe$^{3+}$) in aqueous solution.

In accordance with the present invention, there are provided methods for the in vivo reduction of cyanide levels in a subject. Invention methods comprise administering to a subject an effective amount of at least one physiologically compatible compound capable of binding cyanide, provided, however, that said compound is not hydroxocobalamin.

Physiologically compatible compounds contemplated for use in the practice of the present invention include chelates of a transition metal (e.g., transition metals such as iron, cobalt, copper, manganese, or the like), i.e., any physiologically compatible derivative of the dithiocarbamate moiety (i.e., (R)$_2$N—C(S)—SH), polyamine-polyacetic acid moieties, oxamine moieties, hydrazone moieties, pyridone moieties, piperazine moieties, quinoline moieties, furildioxime moieties, deferiprone moieties, dimercaptan moieties, ethylene diamine moieties, calcein moieties, and the like.

Dithiocarbamate-containing cyanide scavengers contemplated for use in the practice of the present invention include any physiologically compatible derivative of the dithiocarbamate moiety (i.e., (R)$_2$N—C(S)—SH). Such compounds can be described with reference to the following generic structure:

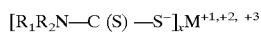

$$[R_1R_2N-C(S)-S^-]_xM^{+1,+2,+3}$$

wherein:

each of $R_1$ and $R_2$ is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, substituted acyl or $R_1$ and $R_2$ can cooperate to form a 5-, 6- or 7-membered ring including N, $R_1$ and $R_2$, x is 1 or 2, and M is optionally present, and when present, is a monovalent cation (when x is 1), or a physiologically compatible divalent or trivalent transition metal cation (when x is 2).

Presently preferred compounds having the above-described generic structure are those wherein:

each of $R_1$ and $R_2$=a $C_1$ up to $C_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl, and M=Fe$^{+2}$ or Fe$^{+3}$.

Especially preferred compounds having the above-described generic structure are those wherein:

$R_1$=a $C_2$ up to $C_8$ alkyl or substituted alkyl, wherein the substituents are selected from carboxyl, acetyl, pyridinyl, pyrrolidinyl, amino, amido, hydroxy or nitro, $R_2$ is selected from a $C_1$ up to $C_6$ alkyl or substituted alkyl, or $R_2$ can cooperate with $R_1$ to form a 5-, 6- or 7-membered ring including N, $R_2$ and $R_1$, and M=Fe$^{+2}$.

The presently most preferred compounds having the above-described generic structure are those wherein:

$R_1$=a $C_2$ up to $C_8$ alkyl or substituted alkyl, wherein the substituents are selected from carboxyl, acetyl, amido or hydroxy, $R_2$=a $C_1$ up to $C_4$ alkyl or substituted alkyl, and M=Fe$^{+2}$.

When $R_1$ and $R_2$ cooperate to form a 5-, 6- or 7-membered ring, the combination of $R_1$ and $R_2$ can be a variety of saturated or unsaturated 4, 5 or 6 atom bridging species selected from alkenylene or —O—, —S—, —C(O)— and/or —N(R)— containing alkylene moieties, wherein R is hydrogen or a lower alkyl moiety.

Monovalent cations contemplated for incorporation into the above compounds include H$^+$, Na$^+$, NH$_4^+$, tetraalkyl ammonium, and the like. Physiologically compatible divalent or trivalent transition metal cations contemplated for incorporation into the above compounds include charged forms of iron, cobalt, copper, manganese, or the like (e.g., $Fe^{+2}, Fe^{+3}, Co^{+2}, Co^{+3}, Cu^{+2}, Mn^{+2}$ or $Mn^{+3}$). In accordance with the present invention, the ratio of dithiocarbamate-species to counter-ion M can vary widely. Thus, dithiocarbamate-containing cyanide scavenger can be administered without any added metallic counter-ion (i.e., $M=H^+$, or a transition metal cation to dithiocarbamate-species ratio of zero), with ratios of transition metal cation to dithiocarbamate-species up to about 1:2 (i.e., a 2:1 dithiocarbamate:transition metal cation complex) being suitable.

As employed herein, "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "alkenyl" refers to straight or branched chain hydrocarbyl groups having at least one carbon-carbon double bond, and having in the range of about 2 up to 12 carbon atoms, and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "aroyl" refers to arylcarbonyl species such as benzoyl and "substituted aroyl" refers to aroyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "acyl" refers to alkylcarbonyl species.

As employed herein, "halogen" refers to fluoride, chloride, bromide or iodide atoms.

Polyamine-polyacetic acid-based cyanide scavengers contemplated for use in the practice of the present invention include any physiologically compatible derivatives of diethylenetriamine pentaacetic acid, diethylenediamine tetraacetic acid, N,N'-bis-(3,4,5-trimethoxybenzyl)ethylene diamine N,N'-diacetic acid, and the like.

Oxamine-based cyanide scavengers contemplated for use in the practice of the present invention include any physiologically compatible derivatives of desferrioxamine, methyl anthranilic desferrioxamine, desferrioxamine B, and the like.

Hydrazone-based cyanide scavengers contemplated for use in the practice of the present invention include any physiologically compatible derivatives of pyridoxal isonicotinoyl hydrazone, salicylaldehyde isonicotinoyl hydrazone, 2-hydroxy-1-naphthaldehyde m-fluorobenzoyl hydrazone, and the like.

Pyridone-based cyanide scavengers contemplated for use in the practice of the present invention include any physiologically compatible derivatives of 1,2-dimethyl-3-hydroxypyrid-4-one, bidentate 3-hydroxypyridin-4-one, and the like.

Piperazine-based cyanide scavengers contemplated for use in the practice of the present invention include any physiologically compatible derivatives of 1,2-bis- (3,5-dioxopiperazine-yl)propane, and the like.

Quinoline-based cyanide scavengers contemplated for use in the practice of the present invention include any physiologically compatible derivatives of 8-hydroxyquinoline, and the like.

Furildioxime-based cyanide scavengers contemplated for use in the practice of the present invention include any physiologically compatible derivatives of 2-furildioxime, and the like.

Deferiprone-based cyanide scavengers contemplated for use in the practice of the present invention include any physiologically compatible derivatives of L1 (i.e., 1,2-dimethyl-3-hydroxy pyrid-4-one), and the like.

Dimercaptan-based cyanide scavengers contemplated for use in the practice of the present invention include any physiologically compatible derivatives of meso-2,3-dimercaptosuccinic acid, 2,3-dimercaptopropane-1-sulphonate, and the like.

Ethylene diamine-based cyanide scavengers contemplated for use in the practice of the present invention include any physiologically compatible derivatives of N,N,N'N'-tetrakis(2-pyridylmethyl) ethylene diamine, and the like.

Calcein-based cyanide scavengers contemplated for use in the practice of the present invention include any physiologically compatible derivatives of 2,2'-bipyridyl, and the like.

In accordance with another embodiment of the present invention, there are provided combination methods for reducing cyanide levels in a subject. Invention methods comprise administering to a subject an effective amount of at least one physiologically compatible compound capable of binding cyanide (as described hereinabove), in combination with at least one of:

alpha-ketoglutaric acid and sodium thiosulfate, hydroxocobalamin, organophosphate antidote (e.g., atropine, oximes, and the like), oxygen therapy, resealed erythrocytes containing rhodanese and sodium thiosulfate, methemoglobin former(s) (e.g., Lily Cyanide Antidote Kit, amylnitrite, sodium nitrite and sodium thiosulfate, primaquine phosphate, 6-methoxy-8-(6-diethylamino-hexylamino) lepidine dihydrochloride, p-aminooctoyl-phenome, p-aminopropiophenone, hydroxylamine, 4-methylaminophenol, and the like), and the like.

In accordance with another embodiment of the present invention, there are provided methods for treating a subject having elevated circulating levels of cyanide, said method comprising administering to said subject an effective amount of at least one physiologically compatible compound capable of binding cyanide, provided, however, that said compound is not hydroxocobalamin.

In accordance with yet another embodiment of the present invention, there are provided methods for reducing the toxicity of cyanide in a subject exposed thereto, said method comprising administering to said subject an effective amount of at least one physiologically compatible compound capable of binding cyanide, provided, however, that said compound is not hydroxocobalamin.

In accordance with still another embodiment of the present invention, there are provided methods for the treatment of cyanide poisoning of a subject, said method comprising administering to said subject an effective amount of at least one physiologically compatible compound capable of binding cyanide, provided, however, that said compound is not hydroxocobalamin.

As readily recognized by those of skill in the art, cyanide toxicity and/or cyanide poisoning is associated with a variety of exposures, e.g., ingestion of certain foods (e.g., extracts of plants containing cyanogenic glycosides, such as cassava) or drugs (e.g., sodium nitroprusside, laetrile), inhalation of industrial gases (e.g., gases produced by electroplating operations), combustion byproducts (e.g., combustion products of polymers prepared from acrylonitrile, methacrylonitrile, allylnitrile, crotononitrile, fumaronitrile, and the like), agents of warfare (e.g., cyanide gas), and the like.

Those of skill in the art recognize that the cyanide scavengers described herein can be delivered in a variety of ways, such as, for example, orally, intravenously, subcutaneously, parenterally, rectally, by inhalation, and the like.

Since individual subjects may present a wide variation in severity of symptoms and each drug has its unique therapeutic characteristics, the precise mode of administration and dosage employed for each subject is left to the discretion of the practitioner. In general, the dosage of cyanide scavenger employed in the practice of the present invention falls in the range of about 0.01 mmoles/kg body weight of the subject/hour up to about 0.5 mmoles/kg/hr. Subjects contemplated for treatment in accordance with the present invention include mammals (such as humans, canines, felines, bovine, ovine, rodents, and the like), fowl (e.g., chicken, turkey, and the like), and so on.

In accordance with still another embodiment of the present invention, there are provided physiologically active composition(s) comprising compounds as described herein in a suitable vehicle, thereby rendering said compound amenable to oral delivery, transdermal delivery, intravenous delivery, intramuscular delivery, topical delivery, nasal delivery, and the like.

Depending on the mode of delivery employed, the cyanide scavenger can be delivered in a variety of pharmaceutically acceptable forms. For example, the scavenger can be delivered in the form of a solid, solution, emulsion, dispersion, micelle, liposome, and the like.

Pharmaceutical compositions of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compound is included in the pharmaceutical composition in an amount sufficient to produce the desired effect upon the process or condition of diseases.

Pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Compounds contemplated for use in the practice of the present invention may also be administered in the form of suppositories for rectal administration of the drug. These compositions may be prepared by mixing the drug with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, it is up to the practitioner to determine a subject's response to treatment and vary the dosages accordingly.

Typical daily doses, in general, lie within the range of from about 10 µg up to about 200 mg per kg body weight, and, preferably within the range of from 50 µg to 10 mg per kg body weight and can be administered up to four times daily. The daily IV dose lies within the range of from about 1 µg to about 100 mg per kg body weight, and, preferably, within the range of from 10 µg to 20 mg per kg body weight.

In accordance with yet another embodiment of the present invention, there are provided compositions comprising a pharmaceutically acceptable carrier containing:

at least one physiologically compatible compound capable of binding cyanide, and at least one of:
  alpha-ketoglutaric acid and sodium thiosulfate,
  hydroxocobalamin,
  organophosphate antidote,
  oxygen therapy,
  resealed erythrocytes containing rhodanese and sodium thiosulfate,
  methemoglobin former(s),
  and the like.

The invention will now be described in greater detail by reference to the following non-limiting examples.

EXAMPLE 1

Figure 1B:
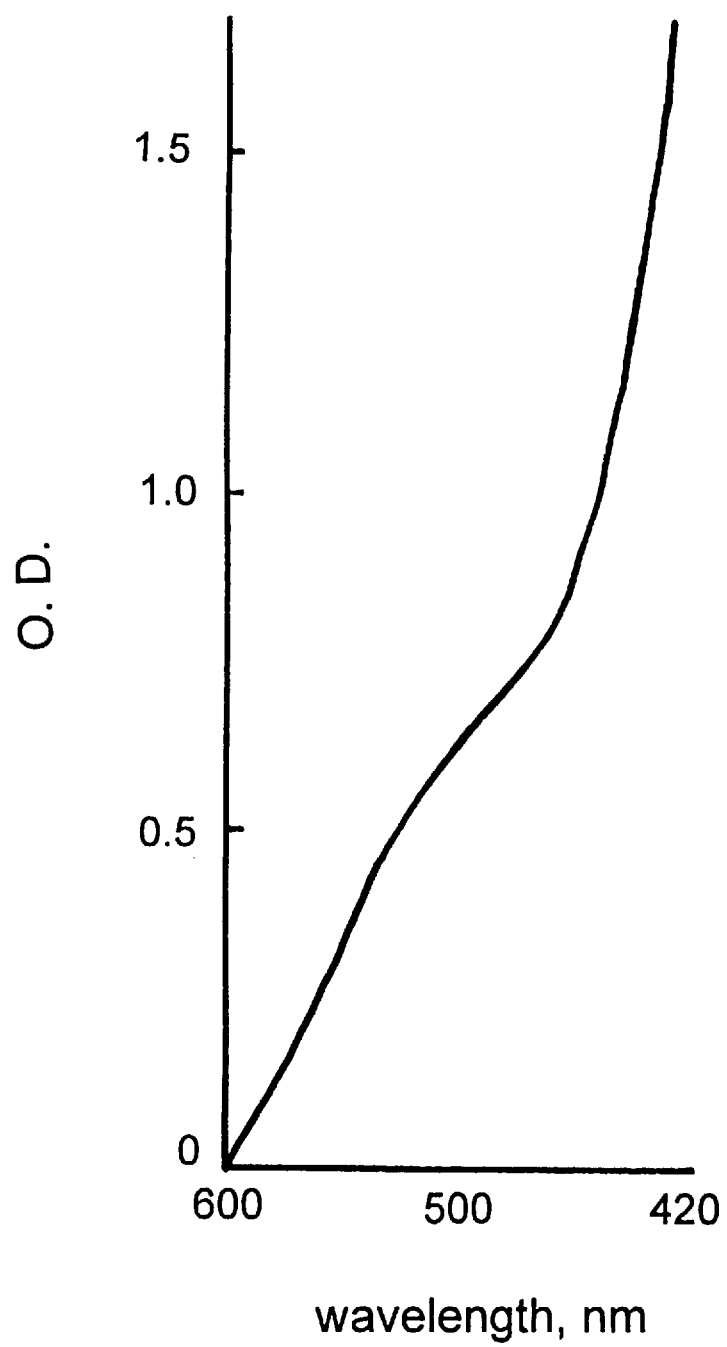

Effect of cyanide binding on the visible spectrum of N-methyl-D-glucamine dithiocarbamate-iron complex N-methyl-D-glucamine dithiocarbamate, synthesized by the method described by Shinobu et al. (Shinobu et al., supra) was highly pure, as determined by elemental analysis and by NMR. FIG. 1A shows the visible spectrum of the [(MGD)$_2$/Fe] complex in water, which displays an intense charge transfer peak at 508 nm. Addition of sodium cyanide to the [(MGD)$_2$/Fe] solution under air-saturated conditions caused the disappearance of the 508-nm charge transfer peak, as shown in FIG. 1B, suggesting a direct binding of cyanide ion to the MGD-Fe complex. This is consistent with the notion that cyanide ion binds to the ferric center of the iron containing complex (see, for example, Solomonson, in Cyanide in Biology (B. Vennesland et al., Eds.), pp. 11–28, Academic Press, New York (1981)). This is the first reported observation of the binding of cyanide to the [(MGD)$_2$/Fe] complex.

EXAMPLE 2

Cyanide toxicity protocol

BALB/c male mice, 20–27 g (Harlan Sprague Dawley, Inc., San Diego, Calif. or Simonsen Laboratories, Inc., Gilroy, Calif.) were acclimated for at least five days. To produce cyanide toxicity, mice were first injected subcutaneously (sc) with 9.6 mg/kg (lethal dose) of KCN in sterile saline (0.9w NaCl). Mice were then treated either intraperitoneally (ip) or intravenously (iv). For ip treatment, mice were injected one minute post-cyanide with either [(MGD)$_2$/Fe] at a 5:1 molar ratio of MGD to Fe or sterile water as vehicle control. For iv treatment, mice were injected within a three minute period post-cyanide with either [(MGD)$_2$/Fe] (5:1 ratio of MGD to Fe) or sterile saline.

To examine binding of CN to [(MGD)$_2$/Fe], a solution containing both KCN and [(MGD)$_2$/Fe] was prepared and mice were given one iv injection of either the KCN/[(MGD)$_2$/Fe] mixture or KCN alone. KCN was injected at a dose of 9.6 mg/kg and [(MGD)$_2$/Fe] at a dose of 100 mg/kg.

Mice were observed for signs of cyanide toxicity, including twitching, labored breathing, and convulsions, for one hour after cyanide injection. The number of surviving individuals was recorded at 24 hours after cyanide injection. Survival data were analyzed by the contingency table method using Fisher's exact test (see, for example, Myers et al., in Anasthesia and Analgesia 84:179–184 (1997)).

TABLE 1

Treatment with [(MGD)$_2$/Fe] Ameliorates Cyanide Toxicity

| Treatment Route | [(MGD)$_2$/Fe][1] Dose (mg/kg) | 24 hr Survival Treated[2] | Control[3] | Ratio [(MGD)$_2$/Fe] to [CN] |
|---|---|---|---|---|
| ip | 400 | 8/12 | 4/12 | 4:1 |
| ip | 200 | 7/10 | 3/10 | 2:1 |
| ip | 100 | 20/30† | 10/30† | 1:1 |
| ip | 50 | 11/20 | 9/20 | 1:2 |
| iv | 100 | 6/9† | 1/9† | 1:1 |

†p ≦ 0.05 by Fisher's exact test.
[1][(MGD)$_2$/Fe] was used at a 5:1 ratio of MGD to Fe. Doses indicated are with respect to MGD.
[2]For ip treatment, mice were treated one minute post-cyanide with the indicated dose of [(MGD)$_2$/Fe]. For iv treatment, mice were treated in the three minute period post-cyanide with the indicated dose of [(MGD)$_2$/Fe].
[3]For ip treatment, mice received 0.1 ml sterile water one minute post-cyanide. For iv treatment, mice received 0.1 ml sterile saline during the three minute period post-cyanide.

Treatment of cyanide toxicity in mice with intraperitoneal injection of [(MGD)$_2$/Fe] at 100 mg/kg resulted in a significant difference in the 24 hour survival rate compared to treatment with vehicle alone (Table 1). Twenty out of thirty mice (20/30) treated with [(MGD)$_2$/Fe] at 100 mg/kg survived for 24 hours compared to ten out of thirty (10/30) in the vehicle control group. The 7-day survival data was similar to that of the 24-hour survival. Higher doses of 200 mg/kg and 400 mg/kg were also effective in improving survival rates compared to controls. The effect of [(MGD)$_2$/Fe] was titratable, since there was no significant difference in the survival rate of [(MGD)$_2$/Fe] treated mice compared to controls at the lower dose of 50 mg/kg. Intravenous treatment with 100 mg/kg [(MGD)$_2$/Fe] also resulted in a significant increase in the survival of cyanide-treated mice at 24 hours compared to saline injected controls.

As demonstrated in FIG. 1, the binding of CN to the [(MGD)$_2$/Fe] complex changed the characteristic charge transfer peak on the visible spectrum of the [(MGD)$_2$/Fe]

complex. The stoichiometric ratio of [(MGD)$_2$/Fe] to CN is calculated with various doses of [(MGD)$_2$/Fe] with respect to Fe content (ranging from 100 to 400 mg/kg) and a constant dose of 9.6 mg/kg KCN. KCN at 9.6 mg/kg is equal to 0.15 mmoles/kg and [(MGD)$_2$/Fe] at 400 mg/kg equal to 0.64 mmoles/kg with respect to Fe content. Assuming that each complex of [(MGD)$_2$/Fe] binds one molecule of CN, [(MGD)$_2$/Fe] doses of 400 mg/kg and 200 mg/kg give rise to a [(MGD)$_2$/Fe] to CN ratio of 4:1 and 2:1, respectively. This indicates that under these experimental protocols an excess of [(MGD)$_2$/Fe] is present compared to CN. Moreover, at a dose of 100 mg/kg [(MGD)$_2$/Fe], the ratio becomes 1:1, indicating that there is one complex of [(MGD)$_2$/Fe] present for each CN molecule. It is therefore not surprising that when the [(MGD)$_2$/Fe] dose is lowered to 50 mg/kg (i.e., when the [(MGD)$_2$/Fe] to CN ratio becomes 1:2), there are no longer enough [(MGD)$_2$/Fe] complexes to bind all the CN molecules. Therefore, as expected, treatment at 50 mg/kg or lower would not be effective and the data indicate that there is no improvement in survival rate of treated mice as shown in Table 1. These results strongly suggest that the effectiveness of [(MGD)$_2$/Fe] in improving the survival of cyanide treated mice is due to the strong stoichiometric binding of [(MGD)$_2$/Fe] to CN.

The evidence for the direct binding of [(MGD)$_2$/Fe] to CN is further supported by the following experiments, which are summarized in Table 2.

TABLE 2

Premixing [(MGD)$_2$/Fe] and KCN Eliminates Cyanide Toxicity

| Treatment Route | [(MGD)$_2$/Fe][1] Dose (mg/kg) | 24 hr Survival [(MGD)$_2$/Fe] + KCN[2] | KCN[3] | Ratio [(MGD)$_2$/Fe] to [CN] |
|---|---|---|---|---|
| iv | 100 | 10/10† | 0/10† | 1:1 |

†p ≦ 0.01 by Fisher's exact test.
[1]Mice were treated with [(MGD)$_2$/Fe] at a 5:1 ratio of MGD to FeSO$_4$. Doses indicated are with respect to MGD.
[2]Mice received injection of 100 mg/kg [(MGD)$_2$/Fe] mixed with 9.6 mg/kg KCN.
[3]Mice received injection of 9.6 mg/kg KCN.

At 9.6 mg/kg, KCN given iv is 100% lethal, as shown in Table 2. However, when [(MGD)$_2$/Fe] at 100 mg/kg is premixed with KCN (9.6 mg/kg) in solution before iv injection, all mice survived and showed no signs of cyanide toxicity (Table 2). As described previously, at these doses, the molar ratio of [(MGD)$_2$/Fe] to KCN is 1:1. Thus, it is conceivable that the direct binding of [(MGD)$_2$/Fe] to CN before injection into mice renders CN harmless.

EXAMPLE 3

Sodium nitroprusside toxicity protocol

BALB/c male mice, 20–26 g (Harlan Sprague Dawley, San Diego, Calif.) were acclimated for at least five days. Mice were injected iv with either a mixture of 10 mg/kg sodium nitroprusside (SNP) plus 100 mg/kg [(MGD)$_2$/Fe] at a ratio of MGD to Fe of 5 to 1 dissolved in sterile water or 10 mg/kg SNP alone. Mice were observed for signs of cyanide toxicity, including twitching, labored breathing and convulsions, for one hour after SNP injection. The number of surviving individuals was recorded at 24 hours after SNP injection. Survival data was analyzed by the contingency table method using Fisher's exact test.

TABLE 3

Treatment with [(MGD)$_2$/Fe] Ameliorates Toxicity of Sodium Nitroprusside

| Treatment Route | [(MGD)$_2$/Fe][1] Dose (mg/kg) | 24 hr Survival Treated[2] | Untreated[3] | Ratio [(MGD)$_2$/Fe] to [CN] |
|---|---|---|---|---|
| iv coinjection | 100 | 8/8† | 0/7† | 5:6 |
| iv coinjection | 20 | 0/5 | 0/10 | 1:6 |

†p ≦ 0.01 by Fisher's exact test.
[1][(MGD)$_2$/Fe] was used at a 5:1 ratio of MGD to Fe. Doses indicated are with respect to MGD.
[2]Mice were injected iv with [(MGD)$_2$/Fe] plus 10 mg/kg SNP.
[3]Mice were injected iv with 10 mg/kg SNP only.

Intravenous injection of SNP at 10 mg/kg resulted in 100% lethality (Table 3). In contrast, all mice which received [(MGD)$_2$/Fe] treatment at 100 mg/kg combined with 10 mg /kg SNP survived. Mice treated with a lower dose of [(MGD)$_2$/Fe] (20 mg/kg) did not show any improvement in survival compared to untreated controls.

Again, assuming that each complex of [(MGD)$_2$/Fe] binds one molecule of CN as previously demonstrated, these results can be predicted when the ratio of [(MGD)$_2$/Fe] to CN is calculated for a constant dose of 10 mg/kg SNP. SNP at a dose of 10 mg/kg is equal to 0.038 mmoles/kg. Because each SNP molecule can release up to 5 molecules of CN when decomposed, 0.038 mmoles/kg of SNP is equal to a maximum of 0.19 mmoles of CN/kg. A dose of 100 mg/kg [(MGD)$_2$/Fe] is equal to 0.16 mmoles [(MGD)$_2$/Fe] with respect to Fe. Thus, at 100 mg/kg [(MGD)$_2$/Fe], the ratio of [(MGD)$_2$/Fe] to CN is 5:6. It would then be expected that most of the CN molecules released from SNP would be bound to [(MGD)$_2$/Fe] and render the CN harmless. On the other hand, at a dose of 20 mg/kg, the ratio of [(MGD)$_2$/Fe] to CN is 1:6. It is therefore not surprising that this dose of [(MGD)$_2$/Fe] did not increase the survival of SNP injected mice because there is not enough [(MGD)$_2$/Fe] to bind all the CN molecules released from SNP. These results further strengthen the notion that [(MGD)$_2$/Fe] is an excellent chelating agent for CN and renders the latter harmless in vivo.

While the invention has been described in detail with reference to certain preferred embodiments thereof, it will be understood that modifications and variations are within the spirit and scope of that which is described and claimed.

That which is claimed is:

1. A method for the in vivo removal of cyanide from a subject, said method comprising administering to said subject an effective amount of at least one physiologically compatible transition metal chelate of a dithiocarbamate-containing cyanide scavenger.

2. A method according to claim 1 wherein said dithiocarbamate-containing cyanide scavenger comprises a dithiocarbamate moiety and, a physiologically compatible di- or trivalent transition metal ion, wherein said dithiocarbamate has the structural formula:

[R$_1$R$_2$N—C(S)S]  (1)

wherein:

each of R$_1$ and R$_2$ is independently selected from a C$_1$ up to C$_{18}$ alkyl, substituted alkyl, cycloalkyl, substituted cycloalkyl, heterocyclic, substituted heterocyclic, alkenyl, substituted alkenyl, alkynyl, substituted alkynyl, aryl substituted aryl, heteroaryl, substituted heteroaryl, alkylaryl, substituted alkylaryl, arylalkyl, substituted arylalkynyl, aroyl, arylalkenyl, substituted arylalkenyl, arylalkynyl, substituted arylalkynyl, aroyl, substituted aroyl acyl, substituted acyl or $R_1$ and $R_2$ can cooperate to form a 5-, 6- or 7-membered ring including N, $R_1$, and $R_2$.

3. A method according to claim 2 wherein said physiologically compatible di- or trivalent transition metal is iron, cobalt, copper or manganese.

4. A method according to claim 2 wherein:

each of $R_1$ and $R_2$=a $C_1$ up to $C_{12}$ alkyl substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl.

5. A method according to claim 1 wherein said dithiocarbamate-containing cyanide scavenger s delivered orally, intravenously, subcutaneously, parenterally, rectally or by inhalation.

6. A method according to claim 1 wherein said dithiocarbamate-containing cyanide scavenger s delivered in the form of a sold, solution, emulsion, dispersion, micelle or liposome.

7. A method according to claim 1 wherein said dithiocarbamate-containing cyanide scavenger is administered in combination with at least one of:

alpha-ketoglutaric acid and sodium thiosulfate, hydroxocobalamin, organophosphate antidote, oxygen therapy, resealed erythrocytes containing rhodanese and sodium thiosulfate, or methemoglobin forming compounds.

8. A method for treating a subject having elevated circulating levels of cyanide, said method comprising:

administering to said subject an effective amount of at least one physiologically compatible transition metal chelate of a dithiocarbamate-containing cyanide scavenger.

9. A method for reducing the toxicity of cyanide in a subject exposed thereto, said method comprising:

administering to said subject an effective amount of at least one physiologically compatible transition metal chelate of a dithiocarbamate-containing cyanide scavenger.

10. A method for the treatment of cyanide poisoning of a subject, said method comprising:

administering to said subject an effective amount of at least one physiologically compatible transition metal chelate of a dithiocarbamate-containing cyanide scavenger.

11. A method according to claim 10 wherein said poisoning is associated with ingestion of food or drugs, or inhalation or industrial gases, combustion byproducts or agents of warfare.

12. A method according to claim 2 wherein:

$R_1$=a $C_2$ up to $C_8$ alkyl or substituted alkyl, wherein the substituents are either carboxyl, acetyl, pyridinyl, pyrrolidinyl, amino, amido, hydroxy or nitro, and $R_2$ is either a $C_1$ up to $C_6$ alkyl or substituted alkyl, or $R_2$ can cooperate with $R_1$ to form a 5-, 6- or 7-membered ring including N, $R_2$ and $R_1$.

13. A method according to claim 2 wherein $R_1$=a $C_2$ up to $C_8$ alkyl or substituted alkyl, wherein the substituents are either carboxyl, acetyl, amido or hydroxy, and $R_2$=a $C_1$ up to $C_4$ alkyl or substituted alkyl.

* * * * *